United States Patent
McPartland

(10) Patent No.: US 8,133,921 B2
(45) Date of Patent: *Mar. 13, 2012

(54) EDIBLE PLANT EXTRACT BASED INSECTICIDAL COMPOSITION

(76) Inventor: Tor McPartland, Carmel Valley, CA (US)

(*) Notice: Subject to any disclaimer, the term of this patent is extended or adjusted under 35 U.S.C. 154(b) by 338 days.

This patent is subject to a terminal disclaimer.

(21) Appl. No.: 12/394,537

(22) Filed: Feb. 27, 2009

(65) Prior Publication Data

US 2009/0176890 A1 Jul. 9, 2009

Related U.S. Application Data

(63) Continuation of application No. 10/235,450, filed on Sep. 4, 2002, now abandoned, which is a continuation-in-part of application No. 09/706,158, filed on Nov. 3, 2000, now Pat. No. 6,784,211, which is a continuation-in-part of application No. 09/218,732, filed on Dec. 22, 1998, now abandoned, which is a continuation-in-part of application No. 08/846,351, filed on Apr. 30, 1997, now abandoned.

(51) Int. Cl.
*A61K 31/015* (2006.01)

(52) U.S. Cl. .................................................. 514/763

(58) Field of Classification Search ............... None
See application file for complete search history.

(56) References Cited

U.S. PATENT DOCUMENTS

| | | | | |
|---|---|---|---|---|
| 3,633,825 A | 1/1972 | Waldron | ............. | 239/135 |
| 3,656,254 A | 4/1972 | Schmedes et al. | ........... | 43/129 |
| 3,930,010 A | 12/1975 | Klopping | ............. | 424/273 |
| 4,279,262 A * | 7/1981 | Horin et al. | ............. | 132/202 |
| 4,379,168 A * | 4/1983 | Dotolo | ............. | 514/763 |
| 4,616,036 A | 10/1986 | Hodgin | ............. | 514/470 |
| 4,933,371 A | 6/1990 | Hink et al. | ............. | 514/739 |
| 5,085,849 A | 2/1992 | Sampson et al. | ........... | 424/45 |
| 5,118,506 A | 6/1992 | Eichoefer | ............. | 424/196 |
| 5,194,264 A | 3/1993 | Van Tonder | ............. | 424/405 |
| 5,441,666 A | 8/1995 | Dotolo | ............. | 252/170 |
| 5,474,712 A | 12/1995 | Dotolo et al. | ........... | 252/550 |
| 5,509,940 A * | 4/1996 | Zbar et al. | ............. | 8/617 |
| 5,653,991 A | 8/1997 | Rod | ............. | 24/406 |
| 5,676,959 A | 10/1997 | Heitz et al. | ............. | 424/405 |
| 5,728,662 A | 3/1998 | Vlasblom | ............. | 510/130 |
| 5,879,674 A | 3/1999 | Black | ............. | 424/93.6 |
| 5,951,991 A | 9/1999 | Wagner | | |
| 5,951,992 A | 9/1999 | Wilkins, Jr. | ........... | 424/405 |
| 6,063,771 A | 5/2000 | Snyder | ............. | 514/31 |
| 6,784,211 B1 * | 8/2004 | McPartland | ............. | 514/763 |
| 2004/0092606 A1 | 5/2004 | McPartland | ............. | 514/762 |

FOREIGN PATENT DOCUMENTS

| | | | |
|---|---|---|---|
| CA | 2060594 | | 8/1992 |
| CA | 2066594 | * | 8/1992 |
| EP | 0 933 026 A1 | | 8/1999 |
| GB | 1603047 | | 11/1981 |
| HU | 211188 A | * | 12/1995 |
| JP | 62-164602 | | 7/1987 |
| JP | 62 164602 | | 7/1987 |
| JP | 01182400 | | 1/1988 |
| JP | 3-104601 | | 5/1991 |
| JP | 7-305049 | | 11/1995 |
| JP | 10-130114 | | 5/1998 |
| JP | 11-279005 | | 10/1999 |
| JP | 2000-515170 | | 11/2000 |
| WO | WO 98/48625 | | 11/1998 |
| WO | WO 01/15534 | | 3/2001 |

OTHER PUBLICATIONS

Insecticides, Entomology-Pests and Insect Control—Insecticides, pp. 1-7.
Piperonyl Butoxide, WHO IPCS INCHEM, Pesticide Residues Series 2, JMPR 1972, pp. 1-9.
R. N. Sherma and K. N. Saxena, "Orientation and Developmental Inhibition in the Housefly by Cedrtain Terpenoids", J. Med. Ent., Nov. 25, 1974, pp. 617-621.
K. A. Powers, et al., ". . . Toxicity of an Insecticidal Spray Containing Linalool, D-Limonene, and Piperonyl Butoxide Applied Topically to Domestic Cats", Vet Hum Toxicol 30, Jun. 1988, pp. 206-210.
3-104601, May 1991, JP—Patent Abstract.
7-305049, Nov. 1995, JP—Patent Abstract.
7-305049, Nov. 1995, JP—Partial translation.
10-130114 A, May 1998, JP—Patent Abstract.
62-164602 A, Jul. 1987, JP—Patent Abstract.
62-164602, Jul. 1987, JP—Partial translation.

* cited by examiner

*Primary Examiner* — Alton Pryor
(74) *Attorney, Agent, or Firm* — Connolly Bove Lodge & Hutz LLP

(57) ABSTRACT

An edible plant-extract-based insecticidal composition comprises d-limonene, a non-toxic hydrophilic solvent, and an amount of a polyethoxylated castor oil sufficient to solubilize the d-limonene in the hydrophilic solvent. The castor oil is both an emulsifier and an active ingredient having insecticidal efficacy. The insecticidal composition is non-toxic to humans and household animals.

9 Claims, No Drawings

EDIBLE PLANT EXTRACT BASED
INSECTICIDAL COMPOSITION

CROSS-REFERENCE TO RELATED
APPLICATIONS

This application is a continuation of U.S. patent application Ser. No. 10/235,450, Sep. 4, 2002, now abandoned which is a continuation-in-part of U.S. patent application Ser. No. 09/706,158, filed Nov. 3, 2000, now U.S. Pat. No. 6,784,211 which is a continuation-in-part of U.S. patent application Ser. No. 09/218,732, filed Dec. 22, 1998, now abandoned which is a continuation-in-part of U.S. patent application Ser. No. 08/846,351, filed Apr. 30, 1997, now abandoned the disclosures of which are incorporated in their entirety herein by reference.

FIELD OF THE INVENTION

The present invention relates to an all-natural, food grade insecticidal composition that is effective in controlling insects including ants, aphids, mealy bugs, white flies, spider mites, leaf hoppers, cabbage loopers, leaf eating beetles and caterpillars, cockroaches, flies, wasps, mosquitoes, wood boring and eating insects, body and head lice and more particularly relates to an insecticidal composition that contains D-limonene, a non-toxic hydrophilic solvent, a non-toxic emulsifying agent, and a preservative, such that the insecticidal composition is an effective residual repellant and contact insecticide but is non-toxic to humans, household animals, and farm animals, and not harmful to landscaping, particularly rose bushes and ornamentals, indoor plants, foundations of structures, soil or the environment.

BACKGROUND OF THE INVENTION

Numerous pesticide and insecticide products are available in the market for killing insects such as ants. However, these products are generally toxic to humans and household animals, and harmful to plants and the environment. Therefore they must be administered with extreme care. This is especially a problem in the termination of ants, cockroaches and the like because they normally appear near food where a careless use of insecticides may cause accidental poisoning of humans and household animals.

Other insecticide products containing D-Limonene disperse the D-Limonene in mineral oil petroleum distillates which may be harmful if accidentally ingested and may cause damage to plants. No emulsifier is used because the D-Limonene is dispersed in oil and not water.

Lice infestation of humans, particularly children, is still treated with compositions that contain the pesticide lindane. Lindane is carcinogenic and an estrogen mimic. There exists a need for a composition which can treat body and head lice but which is safe to use, particularly on children.

U.S. Pat. No. 4,379,168 to Dotolo discloses pesticides containing D-limonene as an insect-killing ingredient along with water-soluble surfactants or emulsifiers, and water. The pesticide compositions are designed for use mainly as a dip to rid small animals of fleas and ticks and as a spray to kill fleas and ticks on small animals. None of the compositions taught by Dotolo contain suitable amounts of emulsifying agent and D-limonene for the purpose of the present invention. None of the compositions taught by Dotolo contain any surfactants or emulsifiers that were selected for their safety. For example, the Kodak Laboratory Chemical Catalog No. 51 indicates that Triton X-100, which is disclosed as an acceptable emulsifier in Dotolo, is irritating to the skin and eyes.

U.S. Pat. No. 3,023,144 to Greathouse, et al. discloses germicides and fungicides containing about 25% by weight D-limonene, about 1% by weight of p-methyl acetophenone, and other unsaturated hydrocarbon cleavage products of D-limonene, up to about 7% by weight concentrated citrus oil foots and from 0.25% up to about 10% by weight salicylic acid. The compositions are used for topical application on humans and animals to control infections of skin and external organs arising from wounds or from infestation by fungi, bacteria, and larvae. Greathouse discloses that the active ingredient for the biocidal activity of the compositions disclosed is not D-limonene but rather compounds such as p-methyl acetophenone, and other unsaturated hydrocarbon cleavage products of D-limonene.

A need exists for an insecticidal composition that kills on contact and controls insects such as ants, aphids, mealy bugs, white flies, spider mites, leaf hoppers, cabbage loopers, leaf-eating beetles and caterpillars, cockroaches, flies, mosquitoes, wood boring and eating insects, wasps, body and head lice by repelling them, and which is non-toxic to humans, household animals, and house plants.

A need also exists for an insecticidal composition that is effective in controlling insects such as ants, aphids, mealy bugs, white flies, spider mites, leaf hoppers, cabbage loopers, leaf eating beetles and caterpillars, spiders, earwigs, slugs and snails, cockroaches, flies, wasps, wood boring and eating insects, body and head lice by killing them, and which is non-toxic to humans, household animals, farm animals, house plants, and soil.

There is also a need for a safe and effective treatment for lice infestation of a human.

A need also exists for an insecticidal composition that contains an insecticide made from a natural substance that is part of and therefore not harmful to landscaping, particularly rose bushes and ornamentals, indoor plants or the environment.

A need also exists for an insecticidal composition that can be used around food, humans, household animals, and farm animals without worry.

There is also a need for an insecticidal composition that can be sprayed on humans and household animals that repels flying insects including flies and mosquitoes. There is also a need for an insecticidal composition that can be sprayed on farm animals and their living environment, including stalls and barns, that repels flying and non-flying insects.

There is also a need for a mosquito repellant for use in yard and barn misting machines and also for mosquito eradication and control for use in truck sprayers in infested areas, for example with West Nile Virus.

There is also a need for a pretreatment insect control that can be applied to soils and structures before construction, can be sprayed during construction on and in walls, foundations, floor and roof areas, and can be sealed or closed in during construction for long-term repellence of insects, including wood boring and eating insects, such as termites, carpenter ants, and carpenter bees.

A need also exists for a safe and effective insecticidal composition mixed with propellants or foaming agents to allow for various applications from an aerosol dispensers.

A need also exists for an insecticidal composition that can be emitted from a mosquito fogging or misting machine.

SUMMARY OF THE PREFERRED
EMBODIMENTS

In accordance with one aspect of the present invention, there is provided a food-grade insecticidal composition that includes an amount of D-limonene sufficient to provide insect control, a non-toxic hydrophilic solvent, and an amount of a non-toxic emulsifying agent sufficient to solubilize D-limonene in the solvent.

Preferably, the inventive composition includes about 1% to about 20% by weight of D-limonene, about 1% to about 25% by weight of the selected non-toxic emulsifying agent, for example Alkamuls EL620, and about 98% to about 55% by weight of the selected non-toxic hydrophilic solvent.

In a preferred embodiment, the inventive composition also includes at least one food-grade preservative, such as sodium benzoate.

Methods of making and using the inventive compositions are also provided.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

The non-toxic insecticidal compositions according to the present invention have a pleasant citrus scent and are suitable for use in any living environment. In particular, the inventive compositions are made only from food-grade ingredients. As used herein, an ingredient or a composition is "food-grade" if it meets the U.S.F.D.A.'s G.R.A.S. (Generally Recognized as Safe) food grade standard. Additionally, in a preferred embodiment of the invention, the inventive compositions are made only from organic ingredients. As used herein, an ingredient or a composition is "organic" if it is made mainly of naturally occurring materials. Thus, the inventive compositions are not only safe and non-toxic to humans, household animals such as dogs, cats, rabbits, birds, lizards, etc. and farm animals, but can also be used near food without any danger of contamination or accidental poisoning, and are safe even if ingested by humans or animals. The inventive compositions will not harm landscaping foliage, indoor plants, soil, or foundations for structures. The inventive compositions can also be applied in stalls and barns without harming animals in such structures. Since the inventive compositions are made of mainly naturally occurring materials, they are not harmful to the environment and do not cause any unwanted pollution. Thus, they can be applied to stalls, barns, and in the walls, roofs, and foundations of structures. The inventive compositions can also be applied using yard and barn misting machines. They are also completely biodegradable.

D-limonene, otherwise known as orange limonene or 1-methyl-4-[(1 methylethenyl]cyclohexene or 4-isopropenyl-1-methyl cyclohexene, has a chemical formula of $C_{10}H_{16}$, a molecular weight of 136.2, and contains 88.1% C and 11.8% H by weight. It occurs in various ethereal oils, particularly in oils of lemon, orange, lime, grapefruit and bergamot. D-limonene can be cold pressed from citrus peels or obtained from steam extraction of citrus peels of orange, lemon, lime, grapefruit and bergamot. Some of the extractions can contain as high as 95% D-limonene. The invention thus provides a valuable use for what would otherwise be a waste product. Distillation of the oils produces technical grades of D-limonene of higher purity, i.e., from about 95% to about 96%. D-limonene has a pleasant citrus scent. It can be suitably used in any living environment.

The D-form of limonene is a liquid having a boiling point of 175.5-176 degrees centigrade. It can be commercially obtained from Lykes Pasco Packing Company (Dade City, Fla.) or Florida Chemical Company (Lake Alfred, Fla.).

The compositions of the present invention allow a user to provide insect control in interior and exterior settings. Insect control can include repelling and/or killing insects, such that less insects are alive or present in a given area than if the compositions of the present invention had not been applied in the area. The inventive compositions control a wide range of insects, including without limitations ants, aphids, mealy bugs, white flies, spider mites, leaf hoppers, cabbage loopers, leaf eating beetles and caterpillars, cockroaches, flies, wasps, mosquitoes, wood boring and eating insects, including termites, carpenter ants, and carpenter bees, and body lice and head lice.

While not limiting the invention by any particular theory, it is believed that the D-limonene acts to soften the waxy coating on the exoskeleton of insects and thereby causes the softened coating to clog the external insect respiratory organs, known as spiracles. The clogged spiracles interfere with the ability of the insect to obtain adequate amounts of oxygen, ultimately resulting in the death of the insect. This invention is therefore also suitable against other pests, besides insects, which would be susceptible to the external effects set forth above.

The inventive compositions include a food-grade, non-toxic hydrophilic solvent. Water is particularly preferred as the solvent as it is edible. Other detoxic or non-toxic hydrophilic solvents, for example, ethanol, dilute acetic acid solutions, hydrogen peroxide, and the like, can also be used.

Useful emulsifying agents include polyethoxylated castor oils. One such emulsifying agent is available commercially under the trade name of Alkamuls EL620 from Rhone Poulenc Co. It is non-toxic to humans, household animals and house plants and landscaping and will not cause skin or eye irritation. Castor oils also improve the insecticidal effect of the formulation. For example, the formulation of castor oil and D-limonene performs as an effective and enduring insect repellant. Castor oils also have the advantage of being an EPA "25b" active ingredient, thereby exempting it from registration as an active ingredient. Other commercially available emulsifying agents that are non-toxic, such as polyoxyethylenesorbitans supplied by ICI Americas or Sigma Chemical Company, may also be suitably used for the present invention provided that they are food-grade. In a preferred embodiment a polyoxyethylenesorbitan monooleate such as Tween 80 may be used.

In general, the emulsifying agent should be present in an amount sufficient to render the D-limonene soluble in the non-toxic hydrophilic solvent. When a polyethoxylated castor oil is used, it should contain sufficient polyethoxylation to render the D-limonene soluble in a non-toxic hydrophilic solvent when the emulsifying agent is used in an amount as disclosed herein. When that solvent is water, the temperature of the water when combined with the other ingredients of the composition should be about 95° F. for optimal emulsification.

In order to provide a reasonable shelf-life to the insecticidal compositions, it is preferable that a preservative be added to the composition. One such suitable preservative is sodium benzoate commercially supplied by Pfizer, Inc. Other commercially available preservatives used for preserving food, as would be known to those of ordinary skill in the art, may also be suitably used.

Preferred embodiments of the inventive insecticidal composition, which are suitable for application as a spray, include about 0.7% to about 20% by weight, more preferably about 0.7% to about 10% by weight, of D-limonene, and even more preferably about 0.775% by weight D-limonene; between about 1% to about 25% by weight, more preferably about 5% to about 15% by weight, of a non-toxic emulsifying agent; about 0.01% to about 5% by weight, more preferably about 0.01% to about 1.0% by weight, of a preservative; and the balance of the selected solvent.

Preferably, the inventive compositions are free of petroleum distillates.

When the novel insecticidal compositions are used indoors as a spray, they should be sprayed preferably from about 6 to about 8 inches away from and directly on insects such as ants, or on insect trails such as ant trails to the source of the insects such as ants (e.g., ant colonies, nests, etc.) and sprayed until visibly wet. Insects are typically killed within minutes of contact with the novel insecticidal compositions.

The insecticidal compositions can be used on the interior surfaces in a building such as counter tops and in food preparation areas. For outdoor use, the insecticidal compositions of the present invention should be applied at the perimeter of a building such as a home, at insect trails such as ant trails, at insect nests, such as ant nests and at doors, cracks, and window frames where insects such as ants may enter the building. It should be applied until visibly wet. It will provide lasting repellent qualities.

The insecticidal compositions can be used as a pretreatment for soils before construction and can be sprayed on and in walls, foundations, floors and roofs so that the composition is sealed or closed in during the construction process. This provides long-term repellence of wood boring and eating insects, including termites, carpenter ants, and carpenter bees. The insecticidal compositions can also be pressure treated on wood, a quality useful in the construction industry. The compositions are also a detoxic alternative to arsenic for pressure treating studs, rafters, joists, and beams.

In a preferred embodiment, a composition having about 0.7% to about 20% by weight of D-limonene is combined with water, forming a treatment formulation. In a more preferred embodiment, a composition having about 0.7% to about 10% by weight D-limonene is combined with water. In a most preferred embodiment, a composition having about 5.8% by weight of D-limonene is combined with water.

Application of the present insecticidal compositions is preferably effected by spraying a treatment formulation of the insecticidal compositions by conventional spray apparatus such as aerosol can bug sprayers and the like. The treatment formulation of the insecticidal compositions can be mixed with propellants or foaming agents to allow for various applications from an aerosol can. Propellants that can be used include CFC, $CO_2$, and nitrous oxide. However, application may also be effected by any means of contacting surfaces to be treated, for example, with a brush which has been dipped in the treatment formulations of the insecticidal compositions. Because the novel insecticidal compositions are non-toxic, they can also be applied with a human hand.

When the present invention is applied to solid surfaces and left to remain there, the residual effect of the insecticidal composition will last for a period of time effectively keeping insects, such as ants, away from the treated area.

The inventive insecticidal compositions can also be applied to a plant, such as a rose bush or other ornamental plant, in order to control insects.

Further embodiments of the inventive compositions can be formulated for use in treating humans, particularly children, infected with lice, particularly head lice. When the novel insecticidal composition is used to treat humans infected with lice, it should be applied to the infected area, such as the scalp and left on for about 5 minutes after which it may be rinsed and preferably shampooed off.

The invention can be made as a concentrate that can be diluted with water. The invention can be used as a paste and be effective in the control of head and body lice.

The treatment formulation of the insecticidal compositions can also be sprayed directly on humans and household animals to repel flying insects, in particular flies and mosquitoes. In a preferred embodiment, a composition of the insecticide having about 0.7% to about 20% by weight, more preferably about 0.7% to about 10% by weight, and most preferably about 1.16% by weight, of D-limonene, is combined with water. A preferred treatment batch is comprised of about six parts water to one part insecticidal composition, A more preferred treatment batch is about five parts water to about one part insecticidal composition, and a most preferred treatment batch is about four parts water to about one part insecticidal composition.

The treatment batch of the insecticidal compositions can also be used as a spray to be applied directly on farm animals to repel insects, in particular flying insects. The treatment batch can also be used in stalls and barns to kill and repel flying and non-flying insects. Preferably, a treatment batch of the insecticide composition of the insecticide having about 0.7% to about 20% by weight, more preferably about 1.16% to about 10% by weight, and even more preferably about 1.6% by weight of D-limonene is used.

Batch treatments of the insecticidal compositions can also be used as a mosquito repellant for use in yard and barn misting machines and also for mosquito eradication and control for use in truck sprayers in infested areas such as an area infested with West Nile Virus. In a preferred embodiment, the concentrated treatment of the insecticidal composition is diluted with water at a ratio of about six parts water to one part composition. In a more preferred embodiment, the concentrated treatment of the insecticidal composition is diluted with water at a ratio of about five parts water to one part composition to create a batch treatment and even more preferably at a ratio of three parts water to one part composition.

The batch treatments of the insecticidal composition can be used in fogging and misting machines for mosquitoes, flies, and treating objects such as pallets. In a preferred embodiment the concentrated treatment of the insecticidal composition is diluted with water at a ratio from about one part insecticidal composition to three parts water, more preferably at a ratio from about one part insecticidal composition to about five parts water, and most preferably at a ratio of about one part composition to about six parts water.

The efficacy of the insecticidal composition can be increased by combining the composition with piperonyl butoxide (PBO). In a preferred embodiment, the insecticidal composition is combined with about 0.05% to about 0.2% PBO (piperonyl butoxide), more preferably with about 0.08% to about 0.15% PBO, and even more preferably with about 0.1% to about 0.12% PBO to increase the efficacy of the insecticidal composition.

Non-limiting examples of the inventive insecticidal composition are set forth below.

EXAMPLE 1

For home, office, school, institutional or industrial applications, indoor and, outdoor (proven effective against ants, roaches and fleas but is a broad based insecticide and repellent):

| | |
|---|---|
| 6 wt % | D-limonene (0.2% impurities in the D-limonene, net active 5.8%) |
| 10 wt % | Alkamuls EL620 (polyethoxylated caster oil) |
| 0.1 wt % | sodium benzoate |
| 83.9 wt % | water. |

The insecticidal composition according to the foregoing specific formulation has a white, opalescent color. Its physical state is a liquid at 25° C. and has a citrus-like odor. It has a boiling point between 99-100° C. and a specific gravity of 0.9753 gm/ml. It is soluble in water and has a pH of 6.1. The flash point of the insecticidal composition is greater than 60° C. It has a viscosity of 1.97 centipoise at 37.8° C.

EXAMPLE 2

For agriculture, on food and ornamental crops (proven effective on aphids and spider mites but useful for many other plant pests):

| | |
|---|---|
| 0.967% to 1.16% | D-limonene (.05% impurities in the d-Limonene, net active 0.725%) |
| 1.667% to 2.8% | Alkamuls EL 620 |
| 0.025% | Sodium Benzoate |
| 95.975% | Water (UV sterilized and particulate filtered to 5 microns) or dionized; |

The foregoing composition is diluted according to four parts water and one part stated composition for ornamentals and five parts water and one part stated composition for crops.

EXAMPLE 3

As a liquid concentrate to make the two previous formulations by simply adding the proper ratio of warm 95° F. water:

| | |
|---|---|
| 18% | D-limonene (0.6% impurities in the D-limonene, net active 17.4%) |
| 30% | Alkamuls EL 620 |
| 0.3% | Sodium Benzoate |
| 51.7% | Water (UV sterilized and particulate filtered to 5 microns) or dionized |

EXAMPLE 4

As a paste for applying to head and body as a treatment for lice (puts lice into a state of morbidity making for easy removal):

| | |
|---|---|
| 24% | D-limonene (0.8% impurities in the D-limonene, net active 23.2%) |
| 40% | Alkamuls EL 620 |
| 0.1% | Sodium Benzoate |
| 35.9% | Water (UV sterilized and particulate filtered to 5 microns) or dionized |

EXAMPLE 5

As a spray that is ready to use for spraying directly on humans, household animals, and on plants for repelling flying insects including flies and mosquitoes

| | |
|---|---|
| 1.2% | D-limonene (.04% impurities in the D-limonene, net active 1.16%) |
| 2.0% | Alkamuls |
| 0.1% | Sodium Benzoate |
| 96.7% | Water (UV sterilized and particulate filtered to 5 microns) or dionized. |

EXAMPLE 6

As a spray for spraying directly on farm animals for repelling insects, including flying insects, and in farm animal living areas for repelling flying and non-flying insects:

| | |
|---|---|
| 1.5% | D-limonene (.05% impurities in the D-limonene, net active 1.45%) |
| 98.4% | Water (UV sterilized and particulate filtered to 5 microns) or dionized. |

EXAMPLE 7

As a pretreatment for a structure, foundation, or soil before construction for repelling wood boring and eating insects:

| | |
|---|---|
| 6.0% | D-limonene (.2% impurities in the D-limonene, net active 5.8%) |
| 10% | Emulsifying Agent |
| 83.9% | Water (UV sterilized and particulate filtered to 5 microns) or dionized. |
| 0.1% | Sodium Benzoate |

What is claimed is:

1. An insecticidal composition consisting of:
d-limonene, a non-toxic hydrophilic solvent, and an amount of a castor oil sufficient to solubilize said d-limonene in said hydrophilic solvent.

2. The insecticidal composition of claim 1, wherein said hydrophilic solvent is water.

3. The insecticidal composition of claim 1, wherein said d-limonene is present in an amount of about 0.7% to about 20% by weight and wherein said castor oil is present in an amount of about 1% to about 25% by weight.

4. An insecticidal composition consisting of:
d-limonene, a non-toxic hydrophilic solvent, an amount of a castor oil sufficient to solubilize said d-limonene in said hydrophilic solvent and a preservative.

5. The insecticidal composition of claim 4, wherein said preservative is a food-grade preservative.

6. The insecticidal composition of claim 4, wherein said preservative is sodium benzoate.

7. The insecticidal composition of claim 4, wherein said d-limonene is present in an amount of about 0.7% to about 20% by weight, wherein said castor oil is present in an amount of about 1% to about 25% by weight, and wherein said preservative is present in an amount of about 0.01% to about 5% by weight.

8. An insecticidal composition consisting of:
d-limonene, a non-toxic hydrophilic solvent, an amount of a castor oil sufficient to solubilize said d-limonene in said hydrophilic solvent, and sesame oil.

9. An insecticidal composition consisting of:
d-limonene, a non-toxic hydrophilic solvent, an amount of a castor oil sufficient to solubilize said d-limonene in said hydrophilic solvent, and piperonyl butoxide.

* * * * *